US012268398B2

(12) United States Patent
Henry et al.

(10) Patent No.: US 12,268,398 B2
(45) Date of Patent: Apr. 8, 2025

(54) CUTTING DEVICE FOR THE PLACEMENT OF A KNEE PROSTHESIS

(71) Applicant: PIXEE MEDICAL, Besancon (FR)

(72) Inventors: Sebastien Henry, La Crau (FR); Pascal Kilian, Amancy (FR); Romain Fissette, Marignier (FR)

(73) Assignee: PIXEE MEDICAL, Besancon (FR)

( * ) Notice: Subject to any disclaimer, the term of this patent is extended or adjusted under 35 U.S.C. 154(b) by 1007 days.

(21) Appl. No.: 17/292,301

(22) PCT Filed: Nov. 8, 2019

(86) PCT No.: PCT/EP2019/080704
§ 371 (c)(1),
(2) Date: May 7, 2021

(87) PCT Pub. No.: WO2020/099268
PCT Pub. Date: May 22, 2020

(65) Prior Publication Data
US 2022/0000491 A1    Jan. 6, 2022

(30) Foreign Application Priority Data
Nov. 12, 2018 (FR) ..................................... 1860423

(51) Int. Cl.
*A61B 17/15* (2006.01)
*A61B 17/16* (2006.01)
(Continued)

(52) U.S. Cl.
CPC .......... *A61B 17/157* (2013.01); *A61B 17/155* (2013.01); *A61B 34/10* (2016.02);
(Continued)

(58) Field of Classification Search
CPC ... A61B 17/154; A61B 17/155; A61B 17/157; A61B 17/15; A61B 17/1662; A61B 17/1664; A61B 17/1668; A61B 17/1675; A61B 17/1682; A61B 17/1739; A61B 17/175; A61B 17/1764; A61B 17/1775; A61B 17/56; A61B 17/58; A61B 2017/564; A61B 2017/567; A61B 2017/568; A61B 34/10; A61B 34/20; A61B 34/25;
(Continued)

(56) References Cited

U.S. PATENT DOCUMENTS

2006/0217733 A1    9/2006 Plassky
2007/0100346 A1*   5/2007 Wyss ..................... A61B 17/15
                                                              606/87
(Continued)

*Primary Examiner* — Marcela I. Shirsat
(74) *Attorney, Agent, or Firm* — Craft Chu PLLC; Andrew W. Chu

(57) ABSTRACT

The cutting device for the placement of a knee prosthesis includes a bracket and a cutting guide mounted with the ability to move on the bracket. The bracket includes a first marker for identifying it and a fixing element for fixing it to a bone. The cutting guide includes a second marker for identifying it and a slot defining a cutting plane suited to guiding a cutting tool. The invention also relates to an assistance device and to a system having the cutting device. The invention finally relates to an assistance method and to a computer program product and to a data recording medium for executing the method.

11 Claims, 6 Drawing Sheets

(51) Int. Cl.
*A61B 17/17* (2006.01)
*A61B 17/56* (2006.01)
*A61B 34/00* (2016.01)
*A61B 34/10* (2016.01)
*A61B 34/20* (2016.01)
*A61B 90/00* (2016.01)
*A61B 90/50* (2016.01)

(52) U.S. Cl.
CPC ............ *A61B 90/39* (2016.02); *A61B 17/154* (2013.01); *A61B 17/1662* (2013.01); *A61B 17/1675* (2013.01); *A61B 17/1739* (2013.01); *A61B 17/1764* (2013.01); *A61B 17/56* (2013.01); *A61B 2017/564* (2013.01); *A61B 2034/101* (2016.02); *A61B 2034/107* (2016.02); *A61B 34/20* (2016.02); *A61B 2034/2046* (2016.02); *A61B 2034/2055* (2016.02); *A61B 2034/2065* (2016.02); *A61B 2034/252* (2016.02); *A61B 2090/3937* (2016.02); *A61B 2090/3983* (2016.02); *A61B 2090/3991* (2016.02); *A61B 90/50* (2016.02)

(58) Field of Classification Search
CPC ... A61B 90/39; A61B 90/50; A61B 2034/107; A61B 2034/101; A61B 2034/2046; A61B 2034/2055; A61B 2034/2057; A61B 2034/2065; A61B 2034/252; A61B 2090/3983; A61B 2090/3904; A61B 2090/3916; A61B 2090/3937; A61B 2090/3991
USPC .......................................................... 606/88
See application file for complete search history.

(56) References Cited

U.S. PATENT DOCUMENTS

| | | | |
|---|---|---|---|
| 2011/0130761 A1* | 6/2011 | Plaskos | A61B 34/10 606/87 |
| 2012/0157887 A1* | 6/2012 | Fanson | A61B 34/25 600/595 |
| 2015/0150641 A1 | 6/2015 | Daon | |
| 2016/0287263 A1 | 10/2016 | Firmbach | |
| 2017/0340367 A1* | 11/2017 | Beger | A61B 17/7083 |
| 2018/0055546 A1* | 3/2018 | Beger | A61F 2/4455 |

* cited by examiner

CUTTING DEVICE FOR THE PLACEMENT OF A KNEE PROSTHESIS

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The invention relates to a cutting device for the placement of a knee prosthesis. The invention also relates to a cutting assistance device comprising such a cutting device. The invention also relates to a method of assisting the fitting of a knee prosthesis and using the said device. The invention finally relates to an assistance system implementing the said method, a computer program product for implementing the said method, and a recording medium comprising the steps of the said method.

2. Description of Related Art Including Information Disclosed Under 37 CFR 1.97 and 37 CFR 1.98

In order to place a knee prosthesis to a subject, it is necessary to first cut the tibia and the femur at their end near the knee.

The bone cut is delicate, the operator must be careful to remove as little bone as possible but must remove enough bone to provide a flat surface and sufficient space to place the prosthesis components. In addition, the angle of the cut is critical. The lack of precision of the operation induces a significant risk of pain felt by the subject, instability, premature wear or dislocation. For this purpose, there are very complex devices using numerous assistance tools: these systems have the disadvantage of being very expensive and not being widely available.

BRIEF SUMMARY OF THE INVENTION

The purpose of the invention is to provide a device and a method for assisting the operator in determining the cutting plane of the tibia or the femur for the placement of a knee prosthesis. In particular, the purpose of the invention is to simplify the determination of the cutting plane by optimizing the accuracy.

According to a first aspect, the invention relates to a cutting device for the placement of a knee prosthesis comprising a bracket and a cutting guide movably mounted on the said bracket, wherein the bracket comprises a first marker for its location and a fixing element for its attachment to a bone and wherein the cutting guide comprises a second marker for its location and a slot defining a cutting plane adapted for guiding a cutting tool.

In one embodiment, the cutting guide is movably mounted on the bracket according to at least one translational degree of freedom.

In one embodiment, the cutting guide is movably mounted on the bracket according to at least two rotational degrees of freedom.

In one embodiment, the cutting guide is movably mounted on the bracket via an articulated assembly allowing the mobility of the cutting guide relative to the bracket.

In one embodiment, the first marker and the second marker comprise a rectangular plane surface comprising at least one pattern.

In one embodiment, the cutting guide comprises a fixing element for attachment to a bone.

According to a second aspect, the invention relates to a cutting assisting device for placing a knee prosthesis comprising at least one cutting device according to the first aspect of the invention and at least one point survey tool comprising a positioning point and a third marker for locating it.

In one embodiment, the assisting device comprises a first cutting device according to the first aspect of the invention designed for cutting a tibia and a second cutting device according to the first aspect of the invention designed for cutting a femur.

According to a second aspect, the invention relates to a method for assisting in the placement of a knee prosthesis.

The method comprises:
  a first phase of positioning a cutting device according to the first aspect of the invention, comprising a cutting guide movable according to three degrees of freedom relative to the bracket of the device,
  a second phase for assisting the positioning of the cutting guide relative to the bracket, comprising
  a step of visualization by a single camera of the first marker of the bracket and the formation of a reference marker defined with respect to the first marker.
  a step of viewing the first marker and the second marker, and
  a step of transmitting and indicating to an operator the relative three-dimensional positioning of the cutting guide and/or its cutting plane with respect to the reference mark.

In one embodiment, the reference marker comprises two reference axes.

In one embodiment, forming the said reference marker comprises the following steps:
  generating a reference point;
  forming a first reference axis passing through the reference point and a predetermined point relative to the first marker;
  forming a second reference axis determined by projecting a known axis of the bracket onto the plane perpendicular to the first reference axis.

In one embodiment, the method is adapted to cut a tibia bone and the reference point is positioned in the mechanical axis of the tibia. In one embodiment, the generation of the reference point is performed by a step of viewing a third marker of a point survey tool relative to the first marker for locating the said reference point.

In one embodiment, the method is adapted to the bone section of a femur and the reference point is positioned in the mechanical axis of the femur. In one embodiment, the generation of the reference point comprises a substep of moving the patient's leg for determination of the center of rotation of the said leg and a substep of viewing multiple images of the first mark during the movement of the leg and a third marker fixed relative to the patient's pelvis.

According to a fourth aspect, the invention relates to a system for assisting in the placement of a prosthesis. The system comprises a cutting device according to the first aspect of the invention, a movable monocular camera, in particular mounted on a pair of glasses or on a portable object such as a telephone, a display means and means for implementing the assistance method according to the third aspect of the invention.

In one embodiment, the viewing step is performed by the said camera and the transmission step is performed by the said display means.

According to a fifth aspect, the invention relates to a computer program product comprising program code instructions stored on a computer-readable medium for implementing the steps of the method according to the third aspect of the invention when the said program is running on a computer or to a computer program product downloadable from a communication network and/or stored on a computer-readable medium and/or computer-executable data carrier, comprising instructions which, when the program is executed by a computer, cause the computer to implement the method according to the third aspect of the invention.

According to a sixth aspect, the invention relates to a data storage medium, readable by a computer, on which is recorded a computer program comprising program code instructions for implementing the method according to the third aspect of the invention or a computer-readable storage medium comprising instructions which, when executed by a computer, lead the latter to implement the method according to the third aspect of the invention.

BRIEF DESCRIPTION OF THE SEVERAL VIEWS OF THE DRAWINGS

The appended drawings represent, by way of example, an embodiment of a cutting device according to the invention and an embodiment of a system according to the invention.

DETAILED DESCRIPTION OF THE INVENTION

Figure 1:
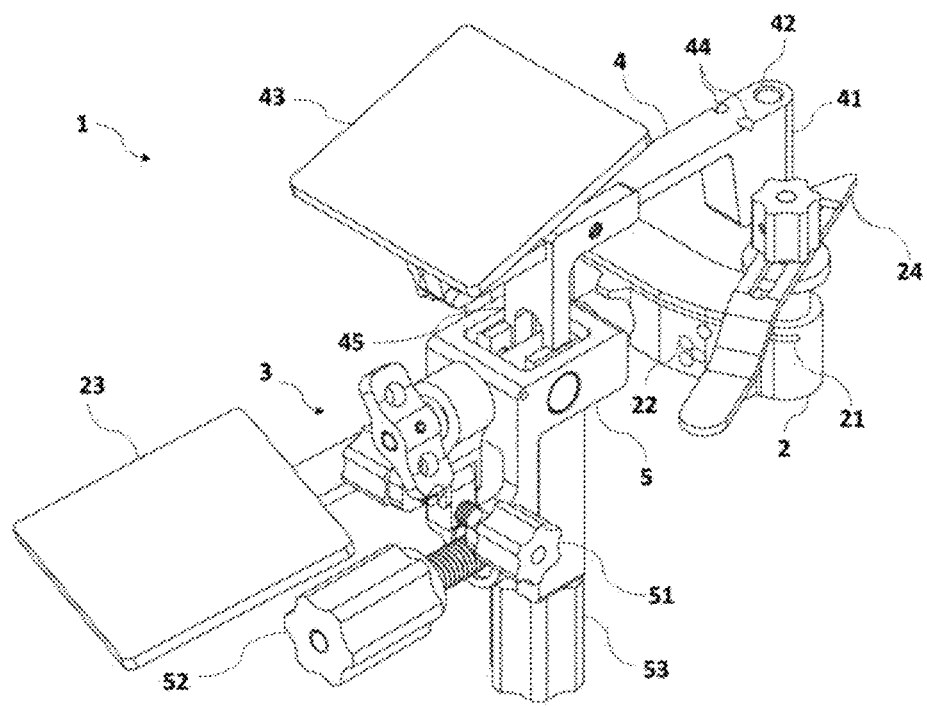
FIG. 1 represents a perspective view of the cutting device according to one embodiment of the invention.

An example of a cutting device 1 for placing a knee prosthesis according to one embodiment of the invention is described below with reference to FIG. 1.

The cutting device 1 comprises a positioning frame 3 and a cutting guide 2. The positioning frame 3 allows the device 1 to be fixed to the bone to be cut, and the movable cutting guide 2 comprises a slot 21 and allows a cutting device to be guided through its slot 21 to perform the bone cutting.

The positioning frame 3 comprises a bracket 4 and an articulated assembly 5. The bracket 4 is designed to be mounted on the bone to be cut. The cutting guide 2 is movably mounted on said bracket 4. The articulated assembly 5 is designed to be movable relative to the bracket 4 and to support the cutting guide 2.

The bracket 4 comprises an attachment means 41 to provide a stable attachment without degrees of freedom between the bracket 4 and the bone to be cut.

As illustrated in FIG. 1, the attachment means 41 may comprise at least a first bore 42 designed to receive a first threaded pin or nail. The bracket 4 is placed against the bone to be cut at an attachment point and the first threaded pin or nail is inserted into the bone through the first bore 42 of the bracket 4.

Advantageously, the bracket 4 allows the positioning frame 3 to be fixed in the vicinity of the cutting plane of the cutting guide 2 described below. In one embodiment, the bracket 4 comprises at least one second bore 44 designed to receive a second threaded pin or nail for securing the bracket 4 to the bone. The longitudinal axis of the at least one second bore 44 is oblique to the longitudinal axis of the first bore 42. In other words, the second bore 44 is designed so that the threaded pin or nail received therein is in an inclined direction relative to the direction of the first screw. This at least one second bore 44 in an inclined direction advantageously allows to block dissociation and/or play of the bracket 4 once mounted on the bone to be cut. The second bore 44 may comprise a smaller diameter than the diameter of the first bore 42.

The bracket 4 is mechanically connected to the articulated assembly 5 of the positioning frame 3. The mechanical connection between the bracket 4 and the articulated assembly 5 comprises at least one degree of freedom. Preferably, the mechanical connection between the bracket 4 and the articulated assembly 5 comprises at least one rotational degree of freedom, preferably two rotational degrees of freedom and one translational degree of freedom.

Preferably, the bracket 4 comprises a mast 45. The mast 45 comprises a longitudinally extending portion designed to receive the articulated assembly 5. The mast 45 may comprise a groove forming a sliding connection with the articulated assembly 5. Preferably, the mast 45 is designed to receive a carriage 531 of the articulated assembly 5 such that the carriage 531 can slide along the longitudinal axis of the mast 45.

Advantageously, the mobility of the cutting guide 2 relative to the mast 4 allows the movement of the cutting guide 2 relative to the bone concerned to be controlled to optimally position the cutting guide 2 for cutting the bone.

In one embodiment, the positioning frame 3 comprises at least one means for controlling the assembly articulated with the bracket. The said control means authorizes the displacement of the articulated assembly 5 with respect to the bracket 4 according to at least one degree of freedom.

More generally, the articulated assembly 5 and the bracket 4 comprise at least two or a plurality of control means each allowing to control the mobility of the articulated assembly 5 or of the cutting guide 2 with respect to the bracket 4 according to a degree of freedom.

The said at least one control means authorizes the displacement of the articulated assembly 5 with respect to the bracket 4 according to at least one degree of freedom in rotation or in translation.

As illustrated in FIGS. 1 to 5, the articulated assembly 5 comprises a first control means 51 authorizing the rotation of the articulated assembly along a first axis B, a second control means 52 authorizing the rotation of the articulated assembly along a second axis C and a third control means 53 authorizing the mobility of the articulated assembly 5 with respect to the bracket by a translation along a third axis A.

The said control means may comprise a locking mechanism and/or a rack.

Figure 2:
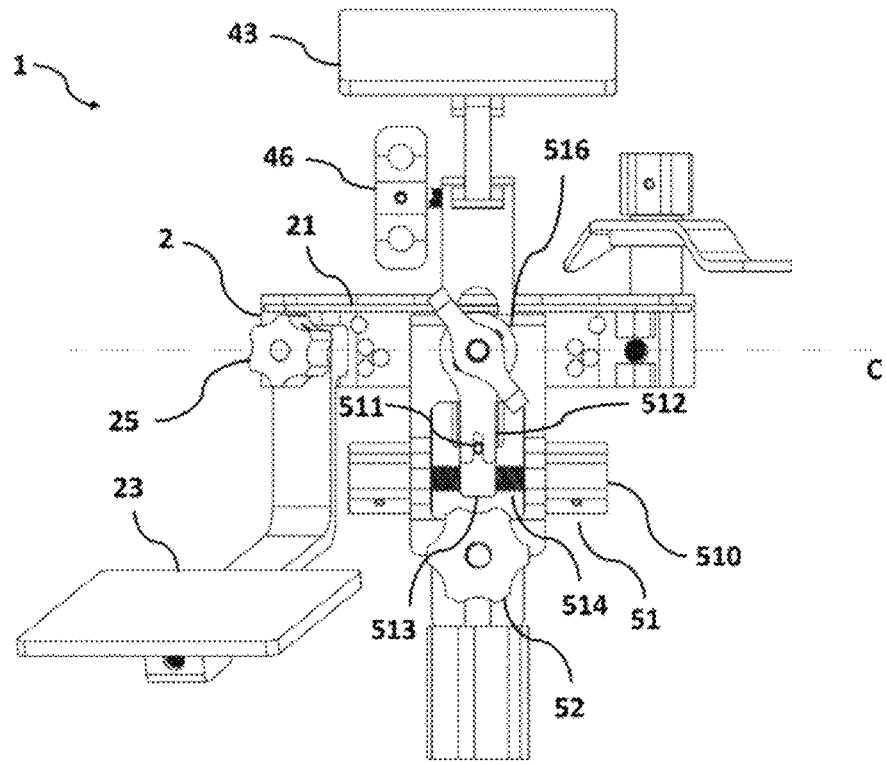
FIG. 2 represents a front elevation view of the cutting device according to one embodiment of the invention.
Figure 3:
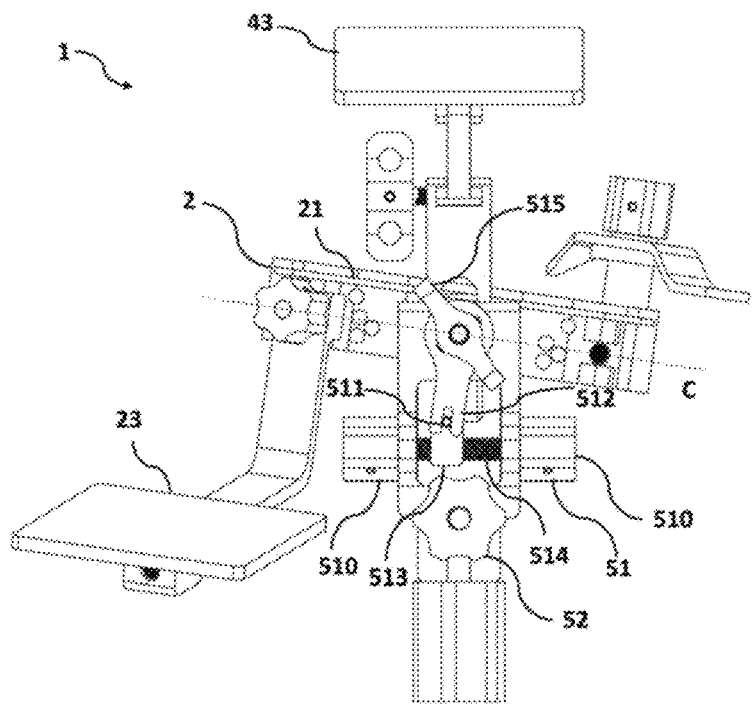
FIG. 3 represents a front elevation view of the cutting device wherein the cutting guide has been moved by a first means for driving the articulated assembly.

As more particularly illustrated in FIG. 2 and FIG. 3, the first control means 51 comprises a drive wheel 510 connected to a screw 514. A movable element 513 is arranged on the thread of said screw 514. When the screw 514 is rotated, the movable element 513 is therefore moved to one side or the other of the screw 514 depending on the direction of rotation of the screw 514. The displacement of the movable element 513 results in a rotation illustrated in FIG. 3 of the articulated assembly 5 along the B axis.

Preferably, the displacement of the movable element 513 along the screw 514 is converted into a rotational displacement of a drive element 512 of the cutting guide 2 by a sliding connection 511 between the movable element 513 and the drive element 512. The said drive element 512 being mechanically connected to the cutting guide 2 via a pivot connection 516, it drives its rotation along a first axis B (shown in FIG. 4) passing through the pivot connection 516.

Preferably, the first control means 51 comprises a drive wheel 510 of the screw 514, very preferably two drive wheels 510 of the screw 514, one on each side of the screw.

Figure 4:
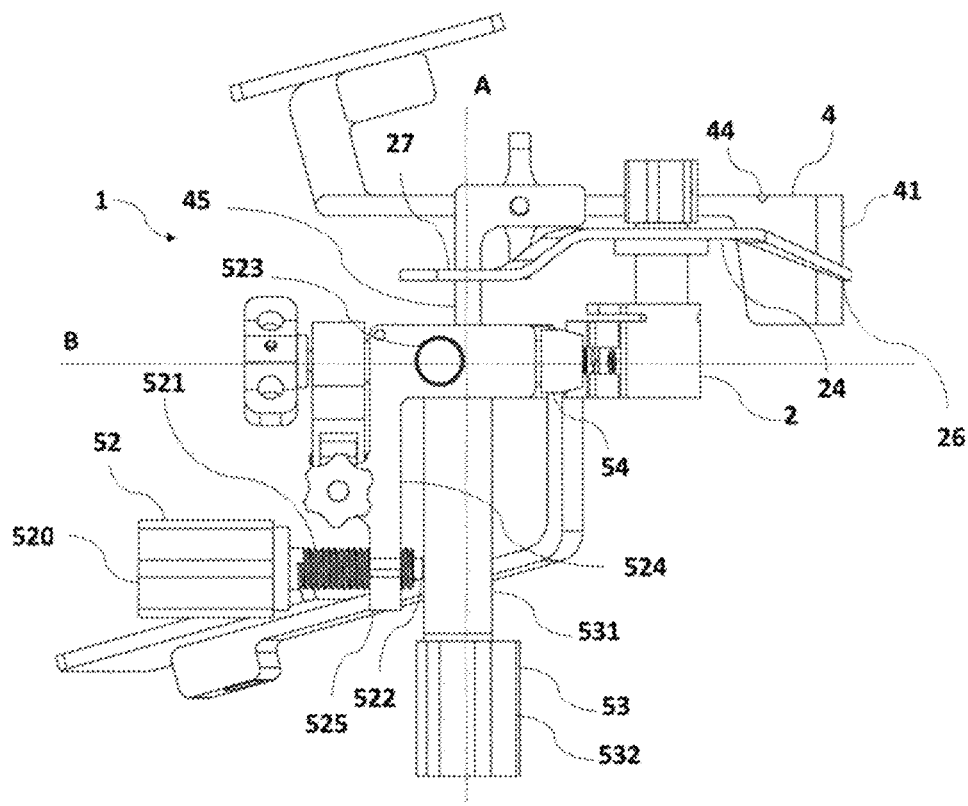
FIG. 4 represents a side elevation view of the cutting device according to one embodiment of the invention.
Figure 5:
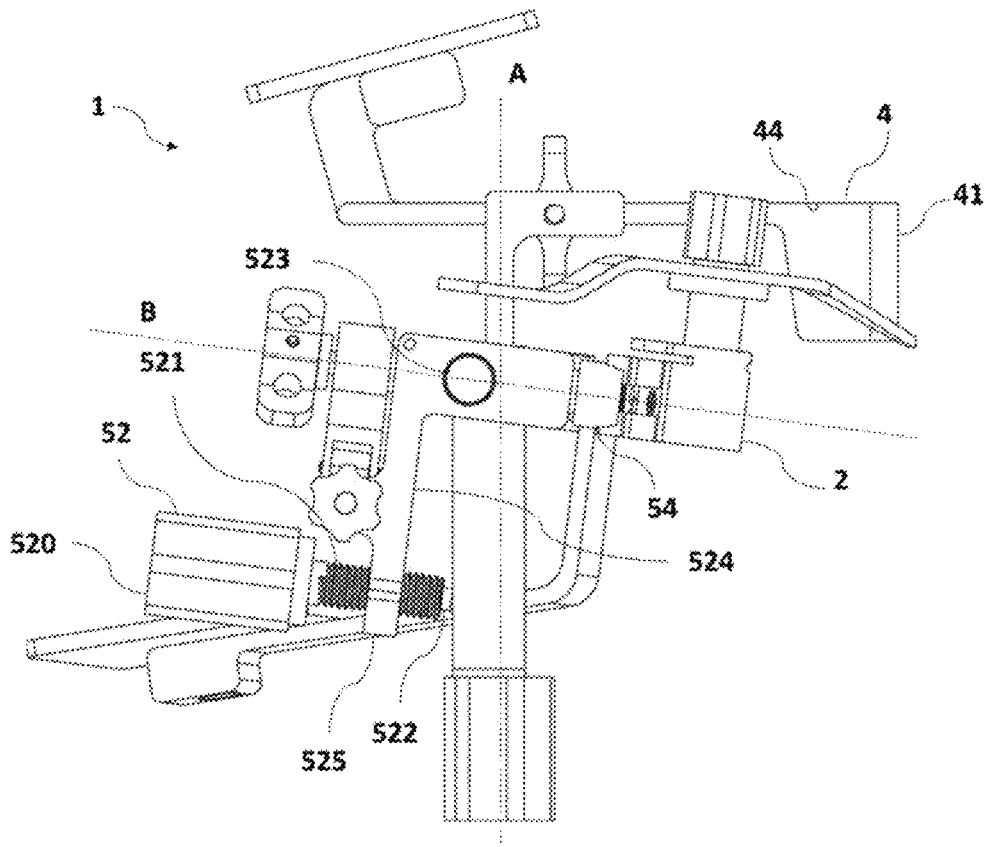
FIG. 5 represents a side elevation view of the device according to one embodiment of the invention wherein the cutting guide has been moved by a second means for driving the articulated assembly.

As more particularly illustrated in FIGS. 4 and 5, the second control means 52 comprises a drive wheel 520 driving a screw 521 integral with the said drive wheel 520. The distal end 522 of the screw 521 is in contact with the carriage 531. The said end 522 is preferably spherical in shape. The said spherical shape is intended to ensure a point connection between the end of the screw 522 and the carriage 45.

The second control means 52 comprises a slope pivot 524. The slope pivot 524 comprises a thread 525. The screw 521 is screwed into the thread 525. More particularly, the thread 525 may comprise a threaded through hole. Thus, rotation of the screw 521 causes longitudinal movement of the thread 525 along the screw 521. The slope pivot 524 further comprises a connection to the cutting guide 2 such that rotation of the slope pivot 524 causes rotation of the cutting guide 2. The slope pivot 524 also comprises a pivot connection 523 to the bracket 4 or to the carriage 531. The said pivot connection 523 is preferably arranged between the thread 525 and the connection to the cutting guide. The longitudinal displacement of the thread 525 along the screw 521 thus causes a rotational movement about the pivot 523 of the slope pivot 524, and thus a rotational movement of the cutting guide 2 along a second axis C illustrated in FIG. 2. The said second axis passing through the pivot 523.

The first control means 51 and the second control means 52 are preferably arranged so that the first axis B and the second axis C, are perpendicular and/or secant at a pivot point 523.

The third control means 53 comprises a sliding connection between the mast 45 of the bracket 4 and the carriage 531 of the articulated assembly 5. The said sliding connection may comprise a means for stopping the said translation. For example, a stop screw 532 arranged at the end of the mast 45.

The stop screw 532 screws onto the end of the mast 45 so as to be displaced along the translation axis A. The stop screw 532 then locks the translation of the carriage 531 in a direction at the desired height or position. In an embodiment not shown, the third control means 53 may comprise a second stop means for blocking the translation of the carriage 531 in a direction opposite to the stop screw 532.

The said sliding connection preferably allows translational movement of the cutting guide 2 along an axis parallel to the longitudinal axis of the first bore 42.

In one embodiment not shown, the positioning frame 3 may also comprise connecting elements forming a rack. The rack comprises a sliding connection between the articulated assembly and the bracket. The sliding connection comprises a first threaded arm and a second arm in sliding connection with the first arm. The rack comprises a gear between the first and second arms, the rotary motion of which about the first threaded arm is converted into a linear motion along the said first arm, the said linear motion of the gear driving the second arm. The rack can also be designed so that one full turn of the gear corresponds to a linear movement of a predefined distance.

Thus, the mobility of the cutting guide 2 relative to the bracket 4 is controlled to allow the operator to position the cutting guide 2 in a precise and stable manner at the desired position and/or orientation.

Preferably, the articulated assembly 5 and the bracket 4 are removable. Indeed, the articulated assembly 5 can be removed from the bracket 4 once the cutting guide 2 is attached to the bone.

Figure 9:
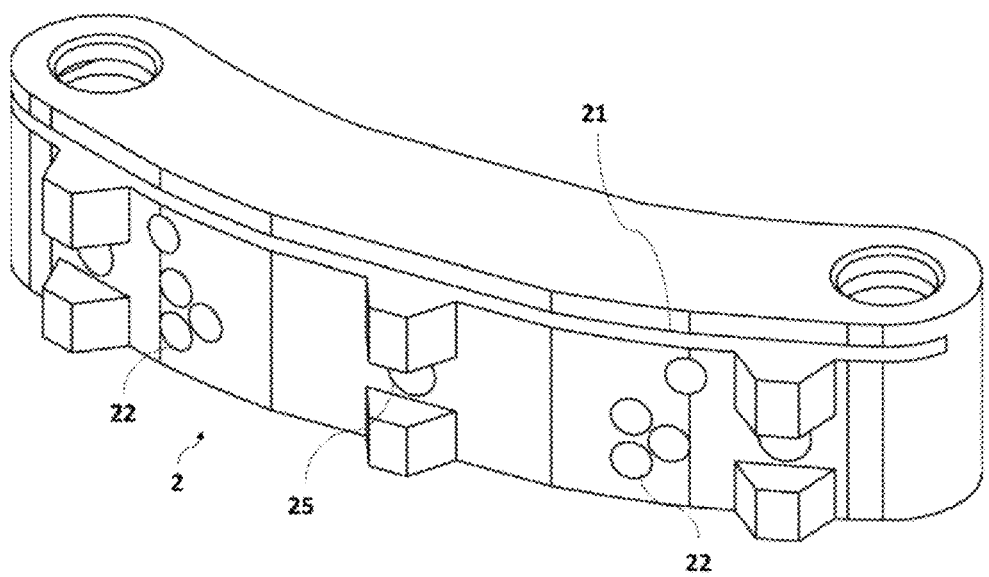
FIG. 9 represents a perspective view of the cutting guide according to one embodiment of the invention.

As shown in FIG. 9, the cutting guide 2 comprises a slot 21. The slot 21 is designed to be in contact with the bone to be cut. It forms a through passage designed to allow a cutting tool to pass through the cutting guide 2 to make the bone cut. The slot 21 thus defines a cutting plane suitable for guiding a cutting tool through the said slot 21. In the continuing description, the plane passing through the said slot will be referred to as the "cutting plane".

The articulated assembly 5 comprises at least one connection element 54 with the cutting guide 2 and the cutting guide 2 comprises at least one connection element 25 complementary to the at least one connection element 54 of the articulated assembly 5, for example, male/female means.

This fixed connection allows the cutting guide to be driven by the articulated assembly 5.

Preferably, this connection is movable so as to remove the articulated assembly 5 from the cutting guide 2 when the cutting guide 2 is attached to the relevant bone. The articulated assembly 5 may comprise a clamping key 515. The said clamping key 515 is integral with a screw (not shown) extending through the mast 45 of the bracket 4 to the connection element 54 or to the cutting guide 2. The purpose of this clamping key 515 is to secure the cutting guide 2 to its connection element 54.

Thus, the operator can remove the positioning frame 3 (the bracket 4 and the articulating assembly 5) from the bone prior to making the bone cut by unscrewing the clamping key 515. In this way, the pin(s) or nail(s) used to secure the positioning frame 3 to the bone are removed and will not interfere with the cut.

In one embodiment, the cutting guide 2 also comprises at least one fixing element 22. The fixing element 22 of the cutting guide allows the cutting guide 2 to be fixed to the bone to be cut. In this manner, once the operator arranges the cutting guide 2 to the desired position via the articulating assembly, the operator can secure the cutting guide 2 to the bone prior to performing the bone cut.

In one embodiment, the cutting guide 2 can be removed from the device.

The fixing element 22 of the cutting guide 2 may comprise a surface designed to be placed on the surface of the bone and a first bore designed to receive a first screw in the same manner as the positioning frame of the bracket. Preferably, the cutting guide attachment element is arranged so that the screw does not interfere with bone cutting.

Preferably, the cutting guide comprises at least two fixing elements, each of which comprises a bore for the passage of a screw to penetrate the bone to be cut. Each bore may extend in a different direction to block the return of the cutting guide.

In one embodiment, the cutting guide 2 is adapted to the morphology of the bone to be cut. In the case of a cutting guide adapted for cutting a tibia, the cutting guide may be asymmetrical.

The cutting guide may further comprise at least one means for attaching a physical probe 24.

In addition, the bracket 4 comprises at least a first position marker 43 for its location and the cutting guide 2 comprises a second position marker 23 for its location.

The first marker 43 and the second marker 23 are designed and arranged to be located by an optical sensor such as a camera.

The image obtained by the camera of a position marker allows its position and orientation to be detected by an algorithm. Each marker has a predefined size, shape and pattern. The algorithm knows the shape, the size and optionally the pattern of the marker. To do this, the algorithm has access to an electronic memory on which digital data representative of the geometry of the elements it analyzes are stored. In particular, by comparing them to the shape, size and pattern of the marker on the image, the algorithm is able to deduce its position and orientation. For example, if a marker comprises a square surface pattern and this same pattern appears trapezoidal on the image, the angles of the trapezoid allow the algorithm to deduce the orientation of the said surface. In addition, the number of pixels between two opposite sides of a square allows the algorithm to deduce the distance between the marker and the camera. Each marker can comprise a different pattern, so the algorithm, by recognizing the pattern, can associate a tool with the position marker, for example, the cutting guide for the second position marker. Since the position markers are attached to the tools without any degree of freedom, the image obtained of the first marker and the second marker can therefore be used to determine the position and orientation of the first and second markers, and therefore of the bracket and the cutting guide respectively.

Indeed, the use of this type of marker makes it possible to improve its position and its three-dimensional orientation in a reference frame of one or more cameras for each image acquisition. This marker can be of different dimensions and geometry.

The pattern can be three-dimensional or two-dimensional. Preferably, the markers comprise a flat surface suitable for receiving, for example by gluing, a label comprising the pattern. In another example, the pattern is screen printed on the said flat surface. The pattern may be in black and white, but the pattern may also be in color.

This pattern differs from those generally used by infrared surgical navigation systems in that it is reusable. Indeed, it is sterilizable by autoclave. This allows a saving of consumables.

The pattern can have simple or complex geometrical shapes. This makes it easier to identify the marker. This also allows for improved estimation of the marker's position and orientation by processing images from one or more cameras.

In fact, the markers according to the embodiment of the invention described herein have a plane rectangular surface comprising at least one pattern.

The particular shape of the first marker and the second marker thus makes it possible to determine the position and orientation of the bracket and the cutting guide, respectively, as described above. This simply constitutes a means for positioning and orienting the first and second markers, and thus the bracket and cutting guide.

An advantage of this particular shape of the markers is also that the estimation of the position and orientation of the bracket and the cutting guide can be done with a single optical sensor such as a camera.

Another advantage is that the image to be processed can be obtained by a single monocular optical sensor, preferably in the visible field, in particular a camera. By "optical sensor in the visible field", we mean that the optical sensor records images visible to the human eye, including so-called "black and white" cameras and so-called "color" cameras. This makes it possible to choose a more economical camera than a system consisting of infrared cameras, generally used by surgical navigation devices.

The optical sensor can be integrated in different devices such as a phone, a tablet, connected glasses or any other system integrating one or more cameras. The set of surgical navigation algorithms can be performed on an embedded platform or on a remote computer.

But the at least one pattern can also be located by the monocular optical sensor used to locate the shape of the markers. By processing the image of the pattern according to a method similar to the processing of the image of the shape of the marker, the position and orientation of the first and second markers, and thus of the bracket and the cutting guide respectively, can also be determined. Thus, one simply constitutes complementary means of positioning and orienting the first and second markers, and thus the bracket and cutting guide.

An advantage of this pattern or patterns is that the estimation of the position and orientation of the first and second markers, and thus of the bracket and the cutting guide, are made by two different means, which further improves the accuracy of positioning and orientation of the first and second markers, and thus of the bracket and the cutting guide.

Thus, with a single camera filming in the visible field, a better positioning and orientation of the first and second marker, and thus of the bracket and the cutting guide, is obtained.

The invention also relates to a cutting assistance device for the fitting of a knee prosthesis, characterized in that it comprises at least one cutting device as described above and at least one point survey tool, described below, comprising a positioning point and a third marker for its location. This cutting assistance device may comprise a first cutting device designed for cutting a tibia and a second cutting device designed for cutting a femur. The assistance device also comprises at least one additional tool for locating a particular position, in particular an anatomical position, which we will call a "point survey tool". The said point survey tool also comprises a third marker for its location, similar to the first marker and/or the second marker. The third marker comprises a particular shape and unique pattern for its identification in an image by the algorithm.

Figure 6:
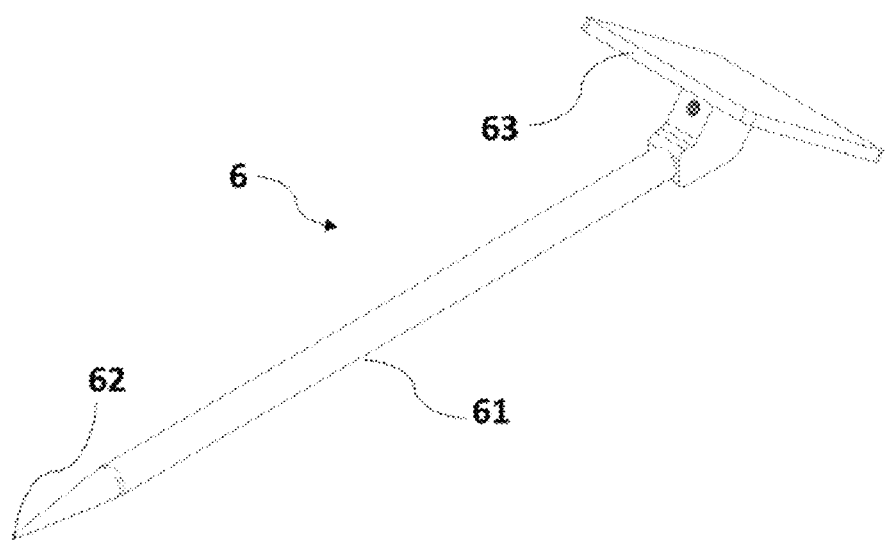
FIG. 6 represents a perspective view of a pointer for implementing the method according to one embodiment of the invention.

In a first embodiment illustrated in FIG. 6, the point finding tool is a pointer 6.

The pointer 6 comprises a shaft 61, a contact point 62 and the third position marker 63. The algorithm uses data representative of the geometry of the pointer 6 so as to know the position of the contact point 62 relative to the third position marker 63. This data can be stored in an electronic memory of the assistance system, which will be described later. Thus, for the generation of a point in a given landmark, it is sufficient to point with the contact point 62 to the point to be recorded, and then to take an image of the third marker 63 and another marker associated with the said landmark formed.

Figure 7:
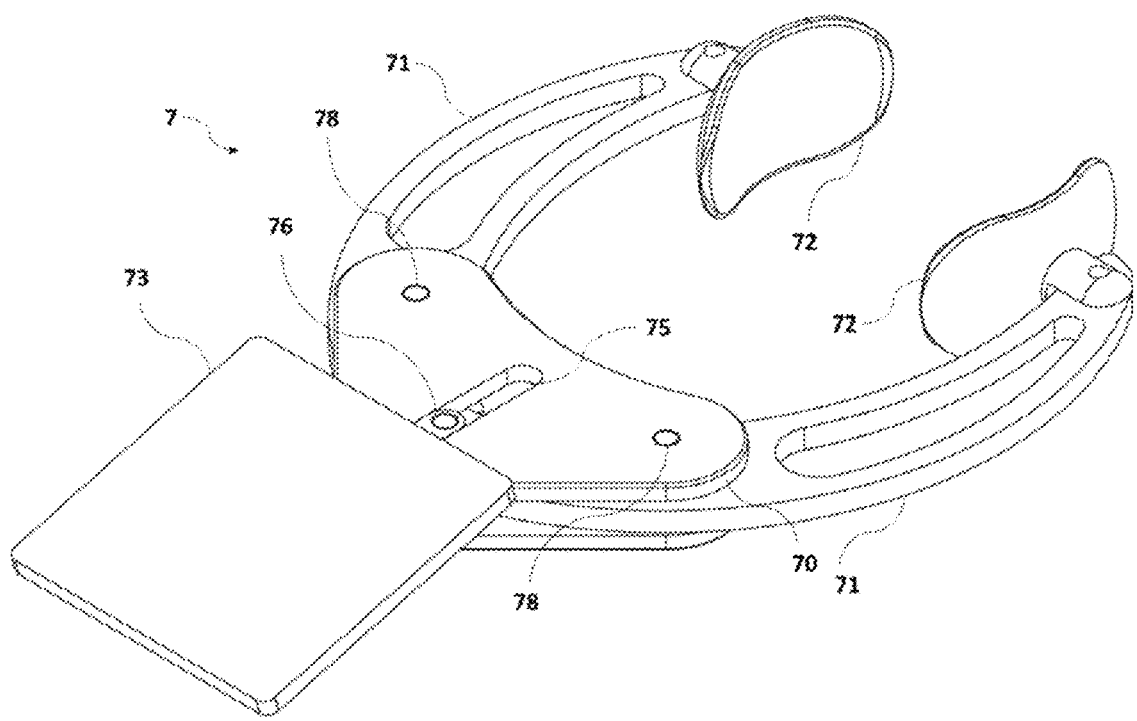
FIG. 7 represents a perspective view of a clamp for implementing the method according to one embodiment of the invention.
Figure 8:
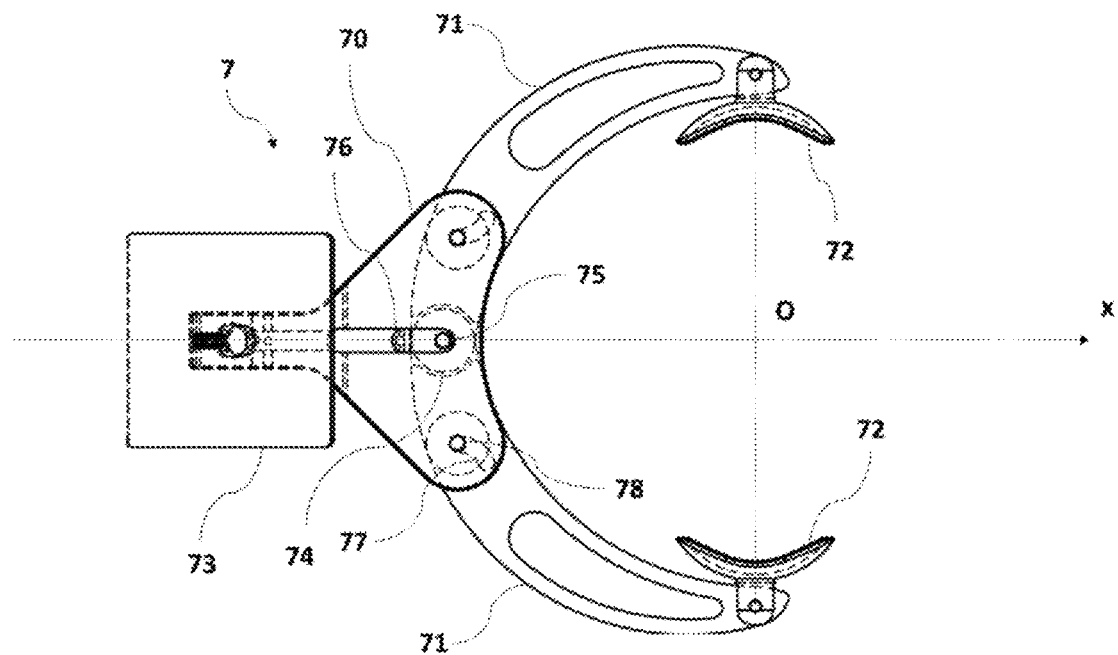
FIG. 8 represents a transparent sectional view of the clamp of FIG. 7.

In a second embodiment illustrated in FIGS. 7 and 8, the point survey tool is a clamp 7.

The clamp 7 comprises a base 70 and two arms 71 movable relative to the base 70. Each arm 71 of the clamp 7 may comprise a pad 72 at its end for positioning. The said pad 72 may comprise a pivotal degree of freedom with the arm 71 of the clamp. In the embodiment, the pad 72 is preferably designed to receive an ankle malleolus.

The base 70 of the clamp 7 comprises a third positioning marker 73. The said marker 73 is integral with the base 70.

The two arms 71 are connected to each other by a pivot connection 74. The said pivot connection comprises a central pinion 75 designed to slide within a central groove 76.

Each arm 71 further comprises a lateral groove designed to cooperate with a lateral pinion 78 of the base 70. As the arm 71 moves relative to the base 70 the lateral pinion 78 slides along the lateral groove 77.

The lateral groove 77 and the central groove 76 are designed in such a way that the projection of the pad 72 according to an axis x parallel to the longitudinal axis of the central groove 76 is constant during the various movements of the arms 71 of the clamp 7.

In addition, the central pivot connection 74 imposes a similar movement of the second arm on the first arm. Thus, the point located in the middle of the segment between the two pads 72 is always located at the same position with respect to the base and with respect to the position marker of the clamp.

When an arm 71 is moved to shorten the distance between the two pads 72, the rotational movement of the arms 71 about the pivot linkage 74 causes the lateral pinions 78 to move along the lateral grooves 77 and the central pinion 75 to move linearly along the linear central groove 76 so that the point O in the middle of the segment between the two pads is stationary with respect to the base 70 and thus with respect to the third marker 73.

Preferably, the clamp 7 comprises a return element (not shown) allowing the central pinion 75 to be held on one of the two ends of the central groove 76, very preferably on the end closest to the lugs. The said element can be a return spring arranged in the groove or a rubber band. This return element allows the return of the ends of the clamps towards each other.

The algorithm uses the position data of a point O in the middle of the segment between the two pads 72 with respect to the third position marker 73. Thus, to generate a point O in a given reference frame, it is sufficient to position the pads 72 and take an image of the third marker 73 and another marker associated with the said given reference frame.

In a third embodiment not shown, the point survey tool comprises a marker attached to a flat surface.

The algorithm uses data from the structure of the survey tool so as to know the position of points on the said plane surface relative to the third position marker.

The invention thus relates to an assisting device comprising a cutting device as described above and a point survey tool as described above.

For the generation of a plane in a given reference frame of the algorithm, it is therefore sufficient to place the flat surface of the survey tool on the plane to be recorded and then to take an image of the third marker and another marker associated with the said given reference frame.

Figure 10:
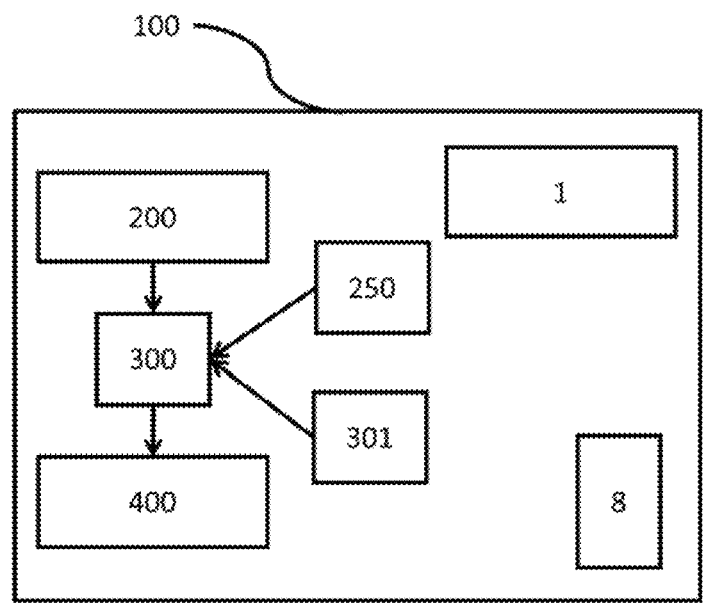
FIG. 10 represents a schematic view of a diagram of an assisting system according to one embodiment of the invention.

An example of an assistance system 100 comprising a cutting device 1 is described below with reference to FIG. 10.

The invention relates to an assistance system 100 comprising a cutting device 1 as described above, an optical capture means 200, in particular a camera, and an information transmission means 400.

Advantageously, the system makes it possible to determine the position of the cutting plane with respect to the bracket or the position of the point to be surveyed O, 62 of the point survey tool by capturing the position markers.

The information transmission means 400 is used to transmit information about the position and orientation of the cutting plane to an operator.

Preferably, the optical capture means 200 is a video capture means so that the position of the cutting guide can be monitored in real time. The optical capture means may be a camera or a still camera.

In one embodiment, the assistance system 100 comprises only one monocular capture means, preferably in the visible field. By "visible field capture means" is meant that the optical capture means records images visible to the human eye including both so-called "black and white" cameras and so-called "color" cameras.

The assistance system 100 also comprises an information transmission means 400. The said information transmission means 400 may be a visual or auditory information transmission means.

The information transmission means 400 may be any means for communicating position and/or orientation information of the cutting plane from the image taken by the optical capture means 200 to an operator.

The information transmission means 400 may be a display means and may comprise a screen, an image projection means, a speaker, an audio headset.

Preferably, the information transmission means 400 comprises a pair of glasses or a monocle to be worn by the operator. The said pair of glasses or monocle may comprise the optical capture means 200, for example in the form of a single camera integrated in the frame or on an arm, and comprising the information transmission means 400, for example in the form of a means for projecting information into the operator's field of view, on a lens of the pair of glasses.

The assistance system 100 also comprises a computer 300 connected to a data storage medium 301, comprising an algorithm for assisting in the fitting of a prosthesis. The computer 300 is connected to the optical capture means to receive the images taken and is connected to the information transmission means to control the said information transmission means.

The assistance system 100 may also comprise an interaction means 250 for the operator to interact with the software. The interaction means 250 may be located on the pair of glasses or on the monocle. This interaction means may comprise a microphone, a control button, a tactile surface, an eye tracking camera.

The interaction means 250 may comprise the pointer 6. In one embodiment, the pair of glasses or monocle displays a graphical interface comprising icons or pictograms. The user can manipulate these icons or pictograms and thereby interact with the software through a pointing device. The pointing device may comprise a pointer 6, a mouse, etc. The user can also interact with the graphical interface through a hand gesture recognition system or accelerometers.

Preferably, the assistance system is activated by a voice command or a body movement, for example a head movement. Once the system is activated, the pair of glasses or monocle displays a graphical interface comprising icons or pictograms. The user can manipulate these icons or pictograms and thus interact with the assistance system software through a pointing device such as the pointer described above or through a hand gesture recognition system.

The graphical interface may comprise virtual interaction buttons. Preferably, the graphical interface comprises a rosette on which the virtual interaction buttons are represented around the center of the said rosette. The user can manipulate the buttons of the rosette and thus interact with the software through a pointing device such as the pointer described above or through a hand gesture recognition system.

The invention also relates to a method of assisting the fitting of a knee prosthesis using a cutting device 1 and/or an assistance system 100 as described above.

The method aims to assist an operator, for example by providing them with information on the position and/or orientation of the cutting plane of the device relative to a formed reference mark. Note that the assistance method of the invention concerns a step upstream of the surgical treatment as such. It only concerns the correct positioning of the assistance tools for the future surgery. Thus, this method is linked exclusively to the correct use of the device, without preventing the surgeon from performing the surgical treatment in a different way without using the said device.

The method comprises a first step of positioning a positioning frame 3 of a cutting device 1 as described above. This step comprises attaching the bracket 4 to a bone to be cut via the at least one fixing element as well as attaching the cutting guide 2 to the articulated assembly 5.

The method then comprises using an optical capture means 200 such as a monocular camera in the visible so that the said camera can detect the first marker of the bracket and the second marker of the cutting guide. An information transmission means 400 is also positioned so that it can transmit information to the user.

The cutting device 1 is placed against the tibia or femur. The cutting device may be placed on either of the aforementioned bones on the articular surface of the knee.

The cutting device is placed against the tibia or the femur so that the cutting plane allows a cut with a thickness between 2 mm and 20 mm, preferably between 6 mm and 10 mm.

The bracket is thus fixed to the bone and the cutting guide remains mobile relative to the bracket and relative to the bone to which the said bracket is fixed.

The method then comprises a second phase of assistance in positioning the cutting guide relative to the bracket, and thus relative to the bone.

For this purpose, the method comprises a step of visualizing the first marker 43 and the second marker 23 by the optical capture means.

The method can implement an algorithm for recognizing a marker in the image taken by the optical capture means. The algorithm can define, thanks to the particular shape of the marker and/or the unique pattern affixed to the marker, the position and orientation in a three-dimensional space of the said marker.

From the viewing step, the method then comprises a landmark formation step.

The formed landmark is a landmark comprising two or three orthogonal reference axes.

The formed landmark comprises a first reference axis, a second reference axis orthogonal to the first reference axis, and optionally a third reference axis orthogonal to the first reference axis and the second reference axis.

Figure 12:
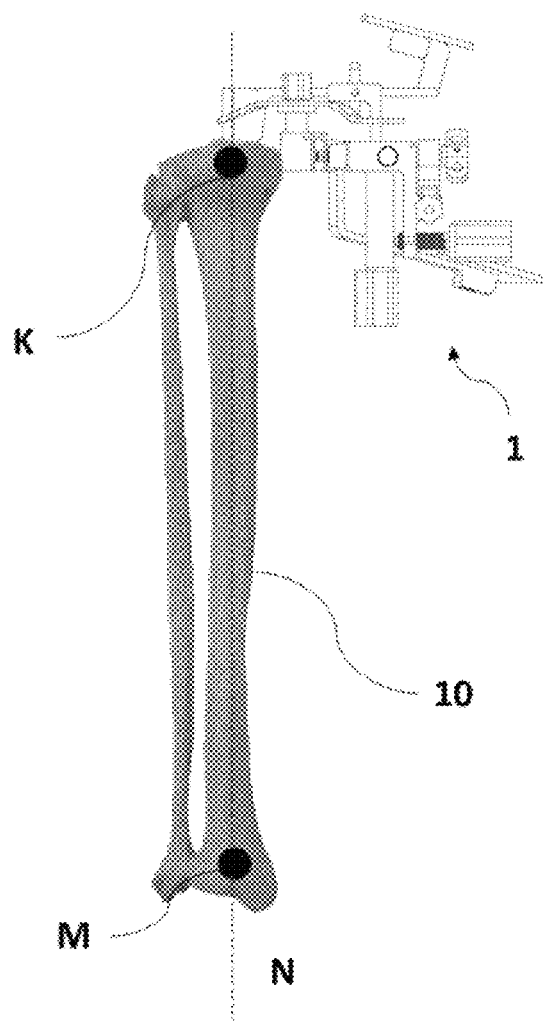
FIG. 12 represents a profile schematic view of a tibia to which a cutting device according to one embodiment of the invention is attached.

The first reference axis N, shown in FIG. 12, is the mechanical axis of the bone to be cut. By mechanical axis, we mean the axis of support of the mechanical forces of the bone in question. The mechanical axis differs from the anatomical or longitudinal axis of the bone extending along the diaphysis of the bone concerned.

The first reference axis N is formed by locating a first point and a second point.

The position of the first point is generated relative to the first marker of the cutting device. Indeed, the bracket of the cutting device occupies a reference position, which is visualized through its first marker. The algorithm can therefore generate the first point representative of the fixing of the bracket to the bone and whose position is fixed relative to the bracket marker. The first point is fixed relative to the bracket. The bracket is therefore designed so that the first point, when the bracket is attached to the bone, passes through the mechanical axis of the bone to be cut.

In the case of the tibia, the position of the second point can be determined using a point survey tool. As illustrated in FIG. 12 on the example of a tibia 10, the first point K is determined by the position and orientation of the first marker.

The mechanical axis of the tibia 10 passes through a point equidistant from the outer point of the left malleolus and the right malleolus of the relevant leg. By outer point, we mean here the point on the surface of the malleolus furthest from the anatomical axis of the tibia.

In one embodiment, the second point M is generated by surveying the outer point of each malleolus of the patient, preferably using the pointer 6 described above. From these two points, the algorithm generates the second point M as the point located at equal distance from the outer point of each malleolus of the patient.

In one alternative embodiment, the clamp 7 as described above is used to determine the second point M. The two pads 72 of the clamp 7 are each placed on the outer point of each malleolus. The second point M then corresponds to the point O equidistant from the two pads 72 of the clamp 7. Such a clamp thus allows to reliably, easily and automatically identify a central (or inner) anatomical point from two lateral supports respectively on two easily locatable anatomical zones, and in a single reading. In the described embodiment, the clamp is designed for two supports on each malleolus of the ankle respectively. Of course, such a clamp could alternatively be used for locating many other anatomical points.

Thus, the invention provides a solution to the technical problem of locating an anatomical point inside the body in a user-friendly and reliable manner.

The solution is based on a clamp, characterized by two articulated arms 71 each comprising a pad 72 allowing positioning on an anatomical zone of the human body. The clamp is equipped with a fixed marker 73 allowing to automatically determine its positioning and to deduce an anatomical interior point, deducible from the two pads 72 of the clamp. In particular, the invention relates to a clamp comprising a base, a first arm and a second arm each comprising a pad, the first arm and the second arm being connected to each other by a movable articulated connection such that movement of one arm causes the movable articulated connection to move along a groove in the base in such a way that the middle of the segment connecting the two arms is immovable relative to the base.

In the case of the femur, the mechanical axis passes through the femoral head of the femur. In order to generate the second point, we use the fact that the femoral head forms the center of rotation of the femur to deduce the position of the second point.

In a first step the user places a position marker on a fixed support relative to the patient's pelvis. Preferably, the position marker is placed on the patient's pelvis but can also be placed on a table on which the patient is lying or on another fixed support in the camera's field of view.

In a second step, the camera takes different images of the fixed position marker and the first position marker. In each image, the patient's knee is moved to a different position.

In each image, the algorithm generates and records a first point on the mechanical axis of the femur by determining the position of the first position marker 43 relative to the fixed position marker.

Next, the algorithm calculates a sphere comprising the set of mechanical axis points. The sphere can be a sphere that is as close as possible to all points via a statistical method.

The algorithm finally determines the center of this sphere as the second reference point.

The position of the second reference point according to the first position marker is thus stored in a memory.

The algorithm then generates the first reference axis relative to the first position marker passing through the first point and the second point.

The second reference axis is generated by projecting a known axis of the bracket 4 onto the plane perpendicular to the first reference axis N. The second reference axis preferably passes through the center of the knee or through the first point K.

The first reference axis N and the second reference axis are thus determined according to the first reference marker 43. On each image taken by the camera from this step, the algorithm is thus able, from the image taken of the first reference marker, to generate an orthonormal reference frame defined by the first and second reference axes.

The intersection of the cutting plane with the first reference axis allows to evaluate the height of the cutting plane with respect to the mechanical axis of the bone to be cut. The cutting plane projected onto the first axis is used to determine the cutting thickness. For this purpose, the algorithm determines the distance between the intersection of the cutting plane with the first reference axis and a thickness reference point.

The thickness reference point is the point located on the articular surface of the knee, preferably at an extremum of the bone surface at the joint. In the example of the femur, the said point is located on the extremum of one of the protruding condyles, i.e., on the most distal point of the protruding curve of a condyle. In the example of the tibia the said point is the point of the bottom of the cup of the tibial plateau or the most distal point of the lateral convex condyle.

In a first embodiment, the thickness reference point is generated by the point survey tool. The user points with the pointer to the extremum of the condyle while the camera captures an image of the pointer position marker and the first position marker. The position of the thickness reference point relative to the first marker is thus recorded.

In a second embodiment, the cutting guide comprises a physical probe 24. The physical probe 24 is designed so that its end 26 can rest on the condyle extremum. For example, as the articulated assembly 5 is moved relative to the bracket 4 via a sliding connection, the projection of the cutting plane onto the mechanical axis N varies, until the end 26 of the probe reaches the condyle extremum. As illustrated in FIG. 4, the probe may comprise two ends 26, 27. The probe is designed so that the first end may rest on an extremum of a concave portion and the second end may rest on an extremum of a convex portion.

The cutting guide is preferably designed so that the intersection of the cutting plane with the first reference axis is at a predetermined distance from the said distal end of the probe and thus from the thickness reference point, preferably about 9 mm. The cutting guide may comprise means for varying this distance between 6 mm and 10 mm.

The marker is thus formed from the first position marker.

Once the marker is formed, the method determines the position and orientation of the cutting plane relative to the said formed marker or reference marker. Preferably, the position and orientation of the cutting guide are controlled by the control means 51, 52, 53 of the positioning frame 3.

The method comprises a step of taking an image comprising the first position marker and the second position marker of the cutting guide.

From such an image and from the orientation of the two markers, this step allows to locate the cutting plane in the formed reference frame.

The algorithm identifies the first marker and deduces the reference marker. By identifying the second marker of the cutting guide in the same image, the position and orientation of the cutting guide or cutting plane in the reference frame is determined.

The method is therefore advantageously compatible with a moving camera or moving optical capture means, due to the fact that the first marker serves as a reference marker for the position and orientation of the cutting plane.

Once the reference marker is determined, and the position and orientation of the cutting plane determined in the said reference frame, the method generates at least one parameter of position and/or orientation of the cutting guide plane relative to the said reference marker.

The parameter may represent an angle of the cutting plane relative to the first reference axis and/or relative to the second reference axis of the reference marker. The step of generating at least one parameter is preferably implemented by the computer.

A first generated parameter may, for example, be the angle or a value dependent on the angle between the cutting plane and the second reference axis, representing the varus/valgus angle.

A second generated parameter may be, for example, the angle or a function of the angle between the cutting plane and the first reference axis, representing the posterior/anterior slope of the articular surface of the knee for the tibia or the flexion/extension parameter of the femur.

A third generated parameter can be the thickness of the cut. The thickness of the cut is determined by the coordinate of the projected plane of the cut on the first reference axis or the distance between this coordinate and the thickness reference point described above.

Thus, when the operator moves the cutting guide thanks to the articulated assembly and thanks to the control means, the camera records the first position marker and the second position marker. From the image taken and the reference marker, the algorithm calculates in real time the position and orientation parameters of the cutting plane.

In one embodiment where the means of transmitting the information comprises the display of the axes forming the reference marker, this display is preferably superimposed on the real image of the knee. This display can be generated with mixed reality glasses.

Finally, the method comprises a step of transmission to an operator of the above-mentioned parameter(s). The transmission is done by the information transmission means 400 of the assistance system 100 according to the invention.

The optical capture means may be mobile. Indeed, since the first marker 43 serves as a reference, the camera can move without unduly disturbing the method. Thus, the method is compatible with the use of a camera disposed in a portable object, such as a cell phone or on glasses.

The invention also relates to a method of tracking a cutting plane according to the second phase of the above-described method.

Once the cutting plane has been placed at the operator's desired location, the operator attaches the cutting guide to the bone with the cutting guide attachment. The positioning frame 3 can then be separated from the cutting guide 2 and the positioning frame 3 removed from the bone. Thus, only the cutting guide 2 remains attached to the bone.

In one embodiment, this step comprises a prior sub-step of transposing the reference mark. For this purpose, the said reference marker, which has been formed relative to the first position marker, is then transposed relative to the second position marker related to the cutting guide which alone remains positioned. In this way, the reference marker is retained by the assistance system, despite the removal of the bracket and the first marker.

After the method has been implemented, the operator can then perform the actual surgical treatment and cut the bone according to the cutting plane using the previously positioned cutting guide.

In one embodiment, once the bone has been cut, the method comprises a step of verifying the cut surface.

The verification step comprises the provision of a point survey tool comprising a marker attached to a flat surface as described above. The surface of the tool is placed on the completed cut surface. The position and orientation of the tool marker relative to the second position marker is used to compare the cut surface to the formed landmark. The algorithm can then calculate the parameters as before. The operator can thus advantageously validate that the cut surface is indeed similar to the cutting plane, as intended.

The assistance system comprises hardware and/or software elements implementing or governing a method for assisting the fitting of a knee prosthesis. In particular, the system comprises hardware and/or software elements implementing the steps of the method of assisting the placement of a knee prosthesis. These various elements may comprise software modules.

For example, the hardware and/or software elements may comprise all or some of the following:
  an optical capture means 200 such as a camera;
  at least one cutting device 1 according to the invention;
  an interaction device 250;
  a computer 300;
  an information transmission means 400;
  a memory or a data recording medium 301;
  at least one point survey tool such as a pointer 6 or a clamp 7.

Figure 11:
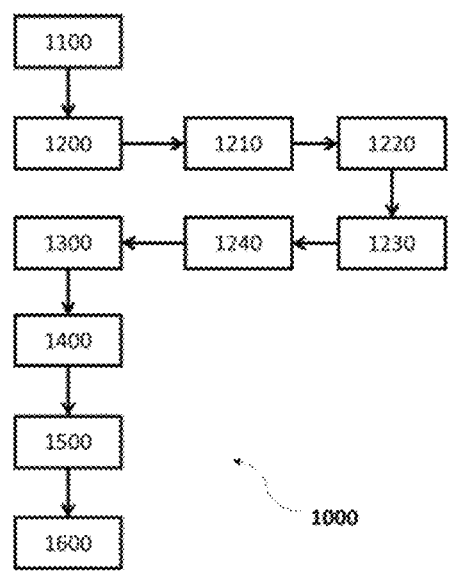
FIG. 11 represents a schematic view of the steps executed by the computer of the assistance system according to one embodiment of the invention.

In one embodiment, the data storage medium 301 comprises instructions 1000 for performing the following steps, shown in FIG. 11:
  receiving a first image 1100 including the first marker;
  forming an orthogonal marker 1200 from the first marker image; and
  receiving a second image 1300 including the first marker and the second marker; and
  determining a cross-sectional plane 1400 in the space of the reference frame formed from the position and orientation of the second marker relative to the first marker in the second image;
  determining at least one position 1500 and/or orientation parameter of the cutting plane relative to the formed marker; and
  transmitting the information 1600 of the at least one determined parameter to the transmission means.

In one embodiment, the step of forming a marker 1200 comprises the following substeps:
  determining 1210 a first point in space relative to the first marker;
  determining 1220 a second point in space on the mechanical axis of the bone to be cut; and
  creating 1230 a first axis passing through the first point and the second point;
  forming 1240 a reference frame comprising the first axis and a second perpendicular axis, in particular formed by the projection of a known axis of the bracket onto the plane perpendicular to the first reference axis.

In a first embodiment adapted to the tibia, the substep of determining a second point comprises the following steps:
  receiving at least one image comprising the first marker and a third marker;
  determining the position of the second point in space relative to the position of the third marker relative to the first marker in the image.

In a second embodiment suitable for the femur, the substep of determining a second point comprises the following steps:
  receiving a plurality of images each including the first marker and another marker;
  determining, from the images, a center of rotation of the first marker relative to the other marker;
  determining the second point as the center of rotation of the first marker.

We claim:

1. A cutting device for placement of a knee prosthesis comprising:
   a bracket being comprised of a first marker, a mast having a longitudinally extended portion, and a bracket fixing element, said first marker having a first rectangular plane surface so as to form a first pattern corresponding to location of said bracket, said bracket fixing element being configured to attach to a bone;
   a cutting guide being movably mounted on said bracket and
   being comprised of
      a second marker and
      a slot, said second marker having a second rectangular plane surface so as to form a second pattern corresponding to location of said cutting guide,
   wherein said slot defines a cutting plane so as to guide a cutting tool,
   wherein said cutting guide is movable mounted on said bracket in at least one translational degree of freedom, and
   wherein said cutting guide is movably mounted on said bracket according to at least two degrees of freedom in rotation; and
      an articulated assembly received on said mast and connected to said cutting guide so as to move said cutting guide relative to said bracket,
   wherein said articulated assembly comprises:
      a first control means for rotation along a first axis;
      a second control means for rotation along a second axis; and
      a third control means for translation along a third axis,
   wherein the first control means comprises:
      a first screw;
      a first movable element on said first screw; and
      a first drive element being in pivoted engagement with said first movable element and being connected to said cutting guide so as to rotate said cutting guide according to rotation of said first screw by said first moveable element,
   wherein the second control means comprises:
      a second screw;
      a drive wheel on said second screw; and
      a slope pivot being in threaded engagement with said second screw and being connected to said cutting guide so as to rotate said cutting guide according to rotation of said second screw by said drive wheel,
   wherein the third control means comprises:
      a carriage in sliding engagement with said mast so as to move said articulated assembly and said cutting guide along said third axis.

2. The cutting device according to claim 1, wherein said cutting guide further comprises a guide fixing element being configured to a corresponding bone.

3. A cutting assistance device for placing a knee prosthesis, comprising:
   the cutting device, according to claim 1; and
   at least one point survey tool comprising a positioning point and a third marker, said third marker having a third rectangular plane surface so as to form a third pattern corresponding to location of said positioning point.

4. The cutting assistance device according to claim 3, further comprising:
   an additional cutting device,
   wherein the cutting device is is configured to cut a tibia, and
   wherein said additional cutting device is configured to cut a femur.

5. A method for assisting the fitting of a knee prosthesis, comprising the steps of:
   positioning the cutting device, according to claim 1,
   wherein said cutting guide is movable in three degrees of freedom with respect to said bracket, and
   positioning said cutting guide relative to said bracket,
   wherein the step of positioning said cutting guide comprises the steps of:
      i. visualizing said first marker by a single camera so as to form a reference marker defined relative to said first marker,
      ii. visualizing said first marker and said second marker so as to determine a relative three-dimensional position of said cutting guide relative to said reference mark, and
      iii. transmitting and indicating to an operator the relative three-dimensional position of said cutting guide relative to reference mark so as to determine a cutting plane of said slot.

6. The method for assisting, according to claim 5, wherein said reference marker comprises two reference axes, and
   wherein the step of visualizing said first marker further comprises the steps of:
      generating a reference point;
      forming a first reference axis passing through said reference point and a predetermined point relative to said first marker; and
      forming a second reference axis determined by projecting a known axis of said bracket onto a plane perpendicular to first reference axis so as to form said reference marker.

7. The method for assisting, according to claim 6, wherein said reference point is positioned in a mechanical axis of a tibia, and
   wherein the step of generating said reference point is comprised of a step of visualizing a third marker of a point survey tool relative to said first marker so as to locate said reference point.

8. The method for assisting, according to claim 6, wherein said reference point is positioned in a mechanical axis of a femur, and
   wherein the step of generating said reference point comprises the steps of:
      moving a leg of a patient so as to determine a center of rotation of said leg; and
      visualizing multiple images of said first marker during movement of said leg and said third marker fixed relative to a pelvis of the patient.

9. A computer program product, comprising:
   program code instructions, stored on a computer-readable medium or downloadable by a computer from a communication network,
   wherein the program code instructions implement the steps of the method for assisting, according to claim 5, when said program code instructions are run on a computer.

10. A computer-readable or computer-readable data storage medium having recorded thereon a computer program comprising:

program code instructions for implementing the method for assisting, according to claim 5.

11. A system for assisting with fitting a prosthesis comprising:
the cutting device, according to claim 1,
a mobile monocular camera mounted on a portable object;
a display means; and
means for implementing an assistance method,
wherein the assistance method is comprised of the steps of:
  positioning the cutting device,
  positioning said cutting guide relative to said bracket,
wherein the step of positioning said cutting guide comprises the steps of:
  i. visualizing said first marker by said mobile monocular camera so as to form a reference marker defined relative to said first marker,
  ii. visualizing said first marker and said second marker so as to determine a relative three-dimensional position of said cutting guide relative to said reference mark, and
  iii. transmitting and indicating to an operator the relative three-dimensional position of said cutting guide relative to reference mark by the display means so as to determine a cutting plane of said slot.

* * * * *